(12) United States Patent
Jackson et al.

(10) Patent No.: US 9,327,085 B2
(45) Date of Patent: May 3, 2016

(54) NEEDLE DISABLING DEVICE USING ELECTRIC CURRENT

(75) Inventors: Kenneth A. Jackson, Glenmont, OH (US); William A. Schureck, Lexingtion, OH (US)

(73) Assignee: SHARPS TERMINATOR, L.L.C., Lubbock, TX (US)

( * ) Notice: Subject to any disclaimer, the term of this patent is extended or adjusted under 35 U.S.C. 154(b) by 239 days.

(21) Appl. No.: 14/003,074

(22) PCT Filed: Sep. 15, 2011

(86) PCT No.: PCT/US2011/051788
§ 371 (c)(1),
(2), (4) Date: Sep. 4, 2013

(87) PCT Pub. No.: WO2013/039502
PCT Pub. Date: Mar. 21, 2013

(65) Prior Publication Data
US 2013/0334175 A1    Dec. 19, 2013

(51) Int. Cl.
*A61M 5/32* (2006.01)
*B02C 19/00* (2006.01)
*B02C 25/00* (2006.01)

(52) U.S. Cl.
CPC .......... *A61M 5/3278* (2013.01); *B02C 19/0075* (2013.01); *B02C 25/00* (2013.01)

(58) Field of Classification Search
CPC ................... A61M 5/3278; A61M 2005/3283; B02C 19/0075; B02C 25/00
See application file for complete search history.

(56) References Cited

U.S. PATENT DOCUMENTS 4,275,628 A * 6/1981 Greenhouse ........ A61M 5/3278
83/167

(Continued)

FOREIGN PATENT DOCUMENTS

| JP | 05-092026 A | * | 4/1993 |
| JP | 2002-085490 A | * | 3/2002 |
| JP | 2005-144085 A | * | 6/2005 |

OTHER PUBLICATIONS

Machine translation of Japan Patent No. 2005-144,085, Jun. 2015.*
Machine translation of Japan Patent No. 2002-085,490, Mar. 2002.*

* cited by examiner

*Primary Examiner* — Geoffrey S Evans
(74) *Attorney, Agent, or Firm* — Jerry Semer

(57) ABSTRACT

A used needle is inserted in a housing of a needle apparatus disabling device. As the needle is pushed downwards sealing a collar opening and bears against a stationary cutter blade. The needle is pushed further into the device where it contacts upper and lower electrodes. An electric current passes through the needle, which causes it to become heated resistively to destruction. A voltage drop between the electrodes is detected by a processor activating a motor driven movable cutter blade which then severs a remaining stub or remnant of the needle portion and simultaneously urges the severed stub downwardly onto the electrodes to ensure its complete destruction. During this process any sparks or airborne contaminants, or combustion gases are prevented from escaping through the opening by the sealing action of the apparatus.

18 Claims, 11 Drawing Sheets

(56) References Cited

U.S. PATENT DOCUMENTS

| | | | | |
|---|---|---|---|---|
| 5,329,087 A * | 7/1994 | Kohl et al. | | 219/68 |
| 5,336,862 A * | 8/1994 | Yelvington | | 219/68 |
| 5,545,869 A * | 8/1996 | Piva | | 219/68 |
| 5,548,095 A * | 8/1996 | Cornell | | 219/68 |
| 5,637,238 A * | 6/1997 | Truesdale et al. | | 219/68 |
| 6,148,742 A * | 11/2000 | Constable et al. | | 110/250 |
| 6,337,454 B1 * | 1/2002 | Walker | | 219/68 |
| 6,545,242 B1 * | 4/2003 | Butler | A61M 5/3278 | 219/68 |
| 2007/0215578 A1 * | 9/2007 | Ito et al. | | 219/68 | ns
NEEDLE DISABLING DEVICE USING ELECTRIC CURRENT

FIELD OF INVENTION

The present invention relates to the field of needle disabling devices, for disabling/destroying a medical needle by current flow through the needle to heat the needle to a temperature at which it becomes disintegrated.

BACKGROUND OF THE INVENTION

Each year a significant number of people, especially health care workers, become infected with blood-borne diseases through the inadvertent stick of a hypodermic needle or other types of needle. A needle stick can lead to a very serious disease. In this connection, because needle sticks provide direct access to the venous systems of individuals, it is possible for a person to contact serious diseases such as AIDS or Hepatitis B through the inadvertent needle stick. The most common times that these needle sticks occur are when the hypodermic needle is being prepared for disposal and during and after actual disposal of said needles. Thus, medical and waste disposal personnel are exposed to the serious risk of injury, infection, disease and even death due to the contamination of medical instruments such as hypodermics that are known in the industry as "sharps." There are many well documented cases of injuries caused by hypodermic needles or "sharps" even while the "sharps" are encased during transportation to a waste site and during the process of destroying or burying the waste. Hypodermic needles have caused injuries in landfills and the needles have been known to wash up on beaches. As long as the needle remains sharp, it is capable of causing injury and infection.

Heretofore the main method of disposing of hypodermic needles has been to deposit the needles in thick-walled plastic containers immediately after use. The containers are then sent to waste processing sites where they are typically incinerated. However, prior to containment, sharps and hypodermic needles may injure or infect individuals attempting to insert the needles into the container, and throughout the process the container remains very susceptible to puncture. There are also several potential health hazards associated with incineration of hypodermic needles due to the toxic byproducts of incineration. Furthermore, the problem remains that the hypodermic needles may escape the medical waste disposal system, exposing many people to health risks.

There have been numerous attempts in the prior art to produce small, light weight needle disposing apparatus that could easily be used by health care professionals. These include U.S. Pat. No. 4,628,169 (Chung Ling), U.S. Pat. No. 48,773,934 (Spinello), U.S. Pat. No. 5,138,124 (Kirk) and U.S. Pat. No. 5,212,362 (Burden).

All of these devices use electrical energy to destroy needles. However, they destroy only a portion of the needle while it remains on the hypodermic. In these prior methods the needle is basically placed in a machine which contains two electrodes. The electrodes make contact with the needle at two different points. Electric current flows through the needle and since the needle is made of stainless steel, it has very high resistance. Thus, the needle heats and disintegrates. This process is almost instantaneous. However, with each of the prior devices a red hot stub is left behind. This stub can cause injury to a person by pricking them, or if touched shortly after disintegration of the needle it can burn them. The license agencies within this area still consider this little stub on the hypodermic as a sharp, as it can penetrate the skin.

Another problem with the prior art devices is that when an individual places the needle up against electrodes, many sparks are formed which can be ejected from the devices causing harm to a user.

A further problem with prior art devices arises from the fact that the entire needle is not fully heated at once. Only the portion between the two electrodes becomes hot enough to be disintegrated. The portion above the top of the electrode becomes warm enough potentially to create an aerosol of any liquid, solid or virus or bacteria left upon the needle. This aerosol may escape the device and become dangerous. Embodiments of the present invention aim to provide a needle disabling device and a method of disabling a needle in which at least some of the abovementioned problems of the prior art are at least partly overcome.

In particular, embodiments of this invention aim to provide a device that will destroy the "sharps" for a hypodermic needle at the point of use. Destroying the hypodermic needle immediately after use greatly reduces the chance of injuries for individuals using the needle, and further, it virtually eliminates the possibility of a person being stuck by the needle in the disposal process or afterward.

Another aim is to provide a device that is easy to use for health care personnel, veterinarians, diabetics, etc. Further aims include providing a device that is portable, battery operable, easy to operate and inexpensive to manufacture.

SUMMARY OF THE INVENTION

According to one aspect of the present invention there is provided a needle apparatus disabling device for disabling a needle apparatus having a body portion and a needle portion, the device comprising a housing for receiving at least a part of a needle apparatus, an electrode assembly for substantially disintegrating a needle portion of the needle apparatus, cutter for severing a needle portion or remnant thereof from a body portion of the needle apparatus and a container for capturing debris, wherein the electrode assembly remains energised after operation of the cutter so as to disintegrate substantially completely the needle portion or remnant thereof.

Preferably the cutter is controlled automatically to sever the needle portion from the body portion, and more preferably the cutter is controlled by an electronic processor which is arranged in use to detect a drop in voltage between electrodes as a needle portion contacts the electrode assembly, and thereby to activate the cutter.

The housing may have an entrance for receiving a needle apparatus, and the entrance preferably comprises an aperture which is dimensioned for a snug fit with a body portion of the needle apparatus when the needle apparatus is pushed into the entrance, so that a seal is formed between the needle apparatus and the aperture, which seal substantially prevents the escape of any sparks or airborne material from the aperture.

The aperture may comprise a substantially circular portion and an elongate slot portion for accommodating needle apparatus having one or more wings.

In a preferred arrangement the entrance comprises a resiliently biased collar member.

The electrode assembly may be arranged to be driven by a series of electrical pulses.

The electrode assembly may comprise at least a pair of electrodes positioned beneath the cutter, and when the cutter severs the needle portion from the body portion of the needle apparatus the severed needle portion may be urged into contact with the electrodes by the cutter.

According to another aspect of the invention there is provided a needle apparatus disabling device for disabling a needle apparatus having a body portion and a needle portion, the device comprising a housing for receiving at least a part of a needle apparatus, a cutter for severing a needle portion from a body portion of the needle apparatus, an electrode assembly for substantially disintegrating a needle portion of the needle apparatus and a container for capturing debris, wherein the electrode assembly is arranged to be driven by a series of electrical pulses.

In accordance with another aspect of the invention there is provided a needle apparatus disabling device for disabling a needle apparatus having a body portion and a needle portion, the device comprising a housing for receiving at least a part of a needle apparatus, a cutter for severing a needle portion from a body portion of the needle apparatus, an electrode assembly for substantially disintegrating a needle portion of the needle apparatus and a container for capturing debris, wherein the housing has an entrance for receiving a needle apparatus, which entrance comprises an aperture which is dimensioned for a snug fit with a body portion of the needle apparatus when the needle apparatus is pushed into the entrance, so that a seal is formed between the needle apparatus and the aperture, which seal substantially prevents the escape of any sparks or airborne material from the aperture.

In accordance with a further aspect of the invention there is provided a needle apparatus disabling device for disabling a needle apparatus having a body portion and a needle portion, the device comprising a housing for receiving at least a part of a needle apparatus, a cutter for severing a needle portion from a body portion of the needle apparatus, an electrode assembly for substantially disintegrating a needle portion of the needle apparatus and a container for capturing debris, wherein the housing has an entrance for receiving a needle apparatus, which entrance comprises an aperture having a substantially circular portion and an elongate slot portion for accommodating needle apparatus having one or more wings.

The invention also provides a method of disabling a needle apparatus comprising a body portion and a needle portion, the method comprising inserting at least a part of the needle apparatus into a housing, substantially disintegrating a needle portion of the needle apparatus by passing an electric current through the needle portion, severing the needle portion from the body portion of the needle apparatus and capturing debris in a container, wherein the method comprises continuing to disintegrate the needle portion or any remnant of the needle portion after the needle portion is severed from the body portion.

Preferably the method comprises automatically controlling the cutter to sever the needle portion from the body portion, and more preferably the method comprises automatically controlling the cutter by an electronic processor which is arranged in use to detect a drop in voltage between electrodes as a needle portion contacts the electrode assembly.

The method may comprise inserting at least a part of the needle apparatus into an entrance of the housing comprising an aperture which is dimensioned for a snug fit with a body portion of the needle apparatus so as to form a seal between the needle apparatus and the aperture which seal substantially prevents the escape of any sparks or airborne material from the aperture.

Preferably the method comprises driving the electrode assembly by a series of electrical pulses.

According to another aspect of the invention there is provided a method of disabling a needle apparatus comprising a body portion and a needle portion, the method comprising inserting at least a part of the needle apparatus into a housing, substantially disintegrating a needle portion of the needle apparatus by passing an electric current through the needle portion, severing the needle portion from the body portion of the needle apparatus and capturing debris in a container, wherein the method comprises driving the electrode assembly by a series of electrical pulses.

According to a further aspect of the invention there is provided a method of disabling a needle apparatus comprising a body portion and a needle portion, the method comprising inserting at least a part of the needle apparatus into a housing, substantially disintegrating a needle portion of the needle apparatus by passing an electric current through the needle portion, severing the needle portion from the body portion of the needle apparatus and capturing debris in a container, wherein the housing has an entrance with an aperture for receiving the needle apparatus, and the method comprises sealing the aperture with the body portion of the needle apparatus when the needle apparatus is pushed into the entrance, so that any sparks or airborne material are substantially prevented from escaping through the aperture.

The invention may include any combination of the features or limitations referred to herein, except a combination of features as are mutually exclusive.

The problem of the hot, sharp stub is addressed by embodiments of the present invention in which the needle is placed within the machine and the needle slides down through the collar, fully placing the whole needle, even the portion that is in the plastic, within the machine. The needle disintegrates as it passes through the electrodes. A cutting device comes across and cuts off the full metal portion of the needle. The remainder of the needle is then disintegrated by electricity. Thus, the needle "nub" or remnant is also/further disintegrated after it is cut from the plastic portion of the hypodermic. This fully cuts off the remainder of the needle and leaves no sharp stub behind.

Embodiments of the invention also address the problem of spark emission in that the needle is not disintegrated until the plastic body of the syringe has become sealed in the insertion hole in the guide. The needle is placed in the machine through a spring-loaded guide collar that seals and the cutting edge fully closes the machine when the needle is disintegrated, thus, no sparks leave the machine.

Sealing the needle off mechanically with the guide, and then disintegrating the full needle at once while exposing entire process to UV light, also eliminates the problem of potentially harmful aerosol emission.

BRIEF DESCRIPTION OF THE DRAWINGS

Preferred embodiments of the present invention will now be described, by way of example only, with reference to the accompanying diagrammatic drawings in which.

DETAILED DESCRIPTION OF THE PREFERRED EMBODIMENT

Essentially, the device is a needle disabling device that destroys needles by heating them with electricity to a temperature at which the needles disintegrate. In embodiments described below the device is housed within a housing having an opening at an upper part. Within the opening is a collar for receiving a portion of a hypodermic syringe to be destroyed. Typical hypodermic syringes comprise a plastic body portion for containing fluid e.g. for injection, and a hollow stainless steel needle portion in fluid connection therewith. The plastic body typically has upper and lower spaced annular plastic ridges of which a first, proximal ridge is located just above the needle portion, and a second, distal ridge is located slightly further from the needle portion.

When the needle of a hypodermic syringe is placed within the opening of the housing, the entire metal portion of the needle, together with a portion of the plastic body of the hypodermic syringe below the second plastic ridge, projects below the collar. When the metallic needle contacts a pair of electrodes a microprocessor determines that a needle has been correctly inserted and triggers a destruction cycle and a small electric motor drives a blade which cuts through the plastic body of the syringe above the needle. The needle portion of the hypodermic needle is pushed between the electrodes, and as a result an electric current is passed through the needle which is sufficient to cause the needle to become disintegrated. The remains of the needle, separated from the rest of the body of the plastic syringe then fall into a removable collection vessel at the bottom of the device where they are repeatedly exposed to light from a germicidal UV lamp. The electric current supplied from rechargeable batteries flows through the needle via the electrodes in a series of pulses controlled by the microprocessor. Supplying current in pulses prolongs the battery life before recharging is necessary. The batteries are preferably rechargeable metal hydride batteries. Within the housing is a small recharging circuit connected to the batteries. The recharging circuit has an external connection for receiving a mains transformer which can be plugged in to charge the batteries. The batteries also provide electrical power to the ultraviolet lamp. After each cycle and when the batteries are being charged the ultraviolet light turns on and kills any germs or bacteria or viruses which may be within the housing.

The process of disintegrating the needle by electricity causes sparks. However, when the needle is placed within the collar, the plastic portion of the needle fully closes the opening of the collar and no sparks escape. The geometry of the collar, the electrodes and the cutting blade together urges the needle in a slightly helical path into contact with the electrodes as the needle is inserted into the device.

Figure 1:
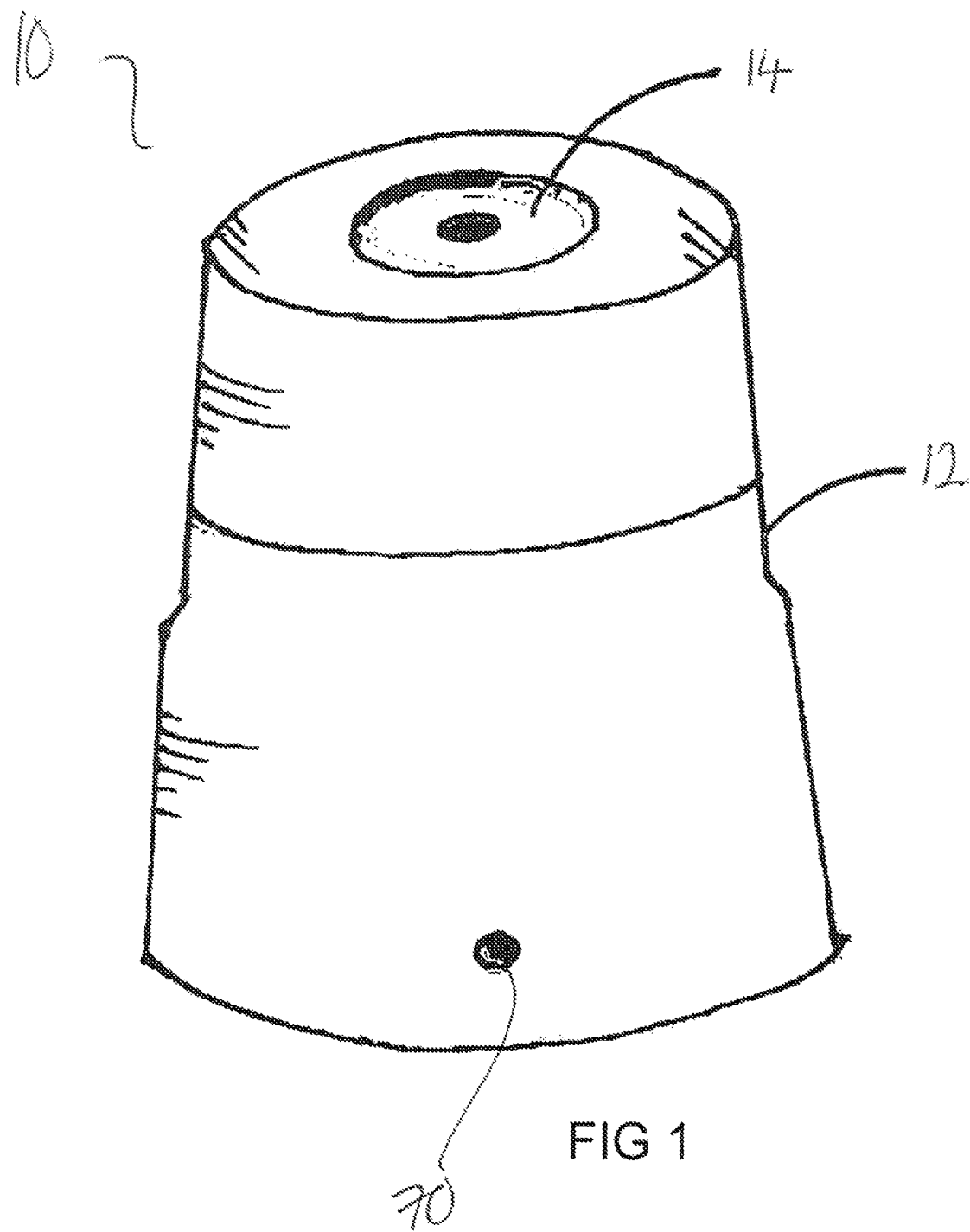
FIG. 1 is a perspective view of a housing of a needle apparatus disabling device, according to an embodiment of the invention.

Turning to FIG. 1, this shows, generally at 10, a needle disabling device in accordance with an embodiment of the present invention. The device 10 comprises a housing 12 which has at an upper part thereof a collar 14 for receiving a needle to be disabled, as will be described below.

Figure 2:
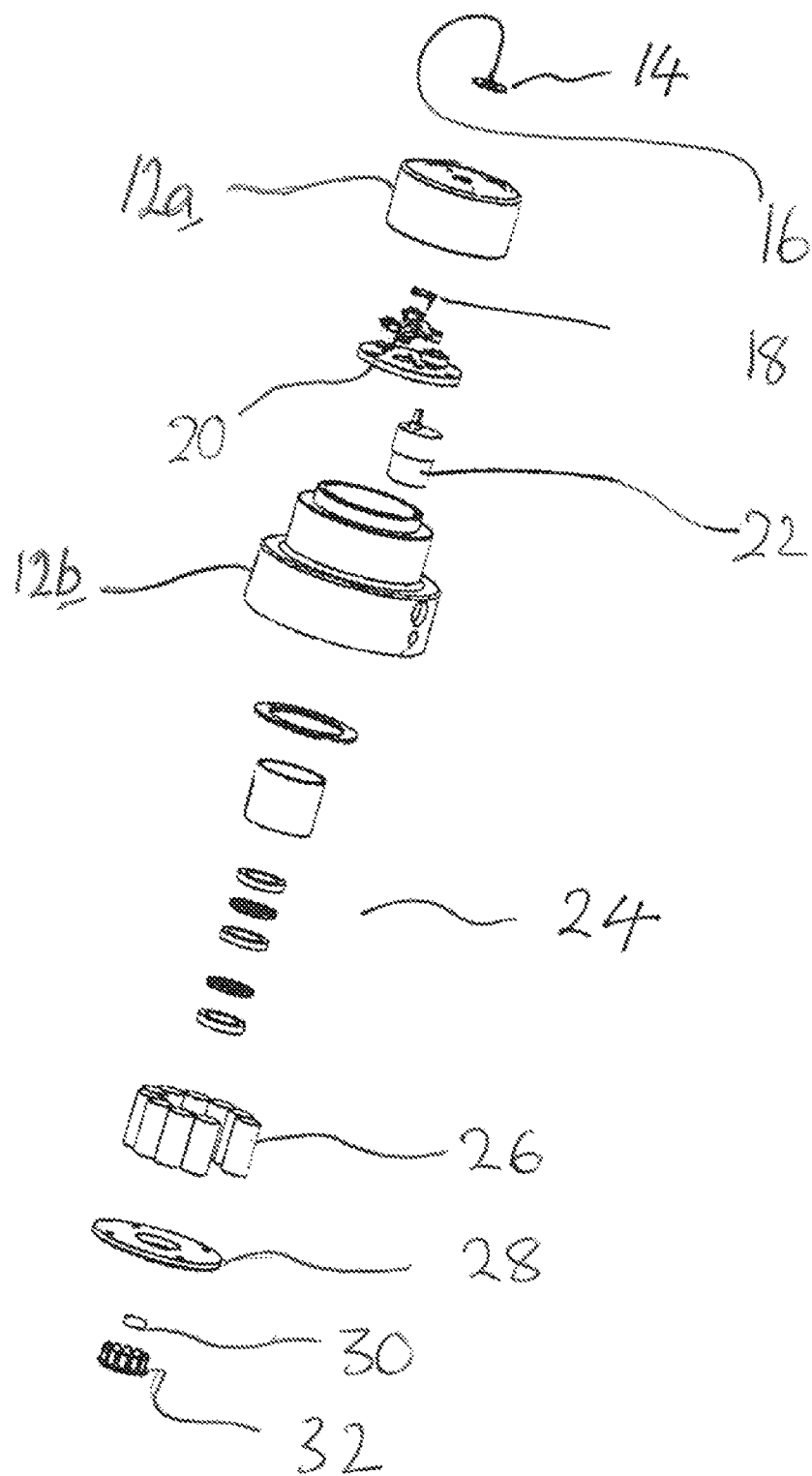
FIG. 2 is an exploded view of the inside of the device.

FIG. 2 is an exploded view of the inner parts of the device with the housing 12 separated into upper 12a and lower 12b parts. At the top of FIG. 2, is the collar 14. Collar 14 fits within the housing 12. In this embodiment the collar has a circular opening 16. However in alternative embodiments (not shown) the opening may include a slot for accommodating needles having one or more wings. Below the opening is a microprocessor 18, a mounting plate 20, a direct-current motor 22, a series of electrodes 24, a battery pack 26, a base plate 28, an ultra-violet lamp 30 and a removable debris container 32.

Figure 3:
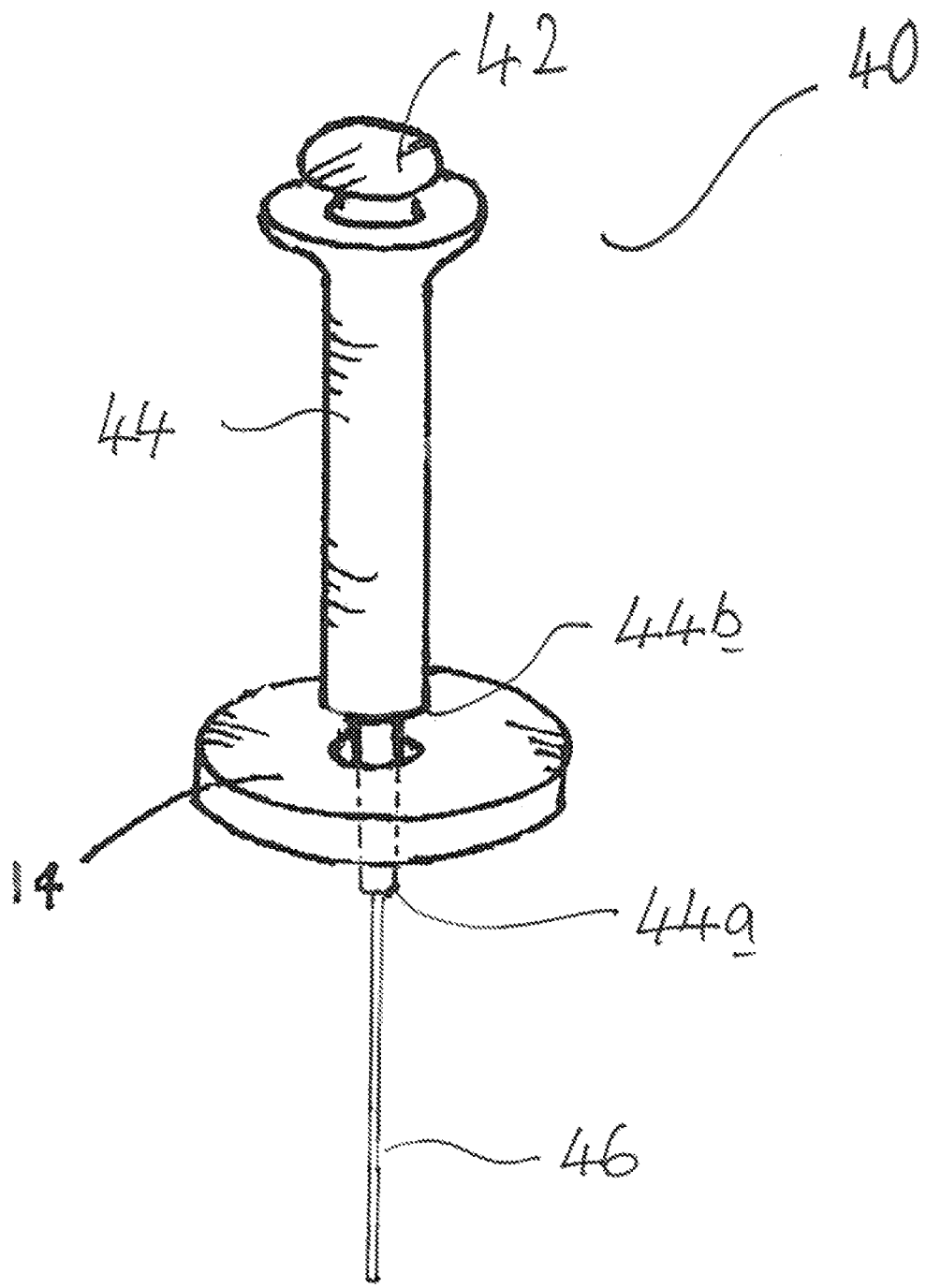
FIG. 3 is a view of a hypodermic needle within a collar.
Figure 4:
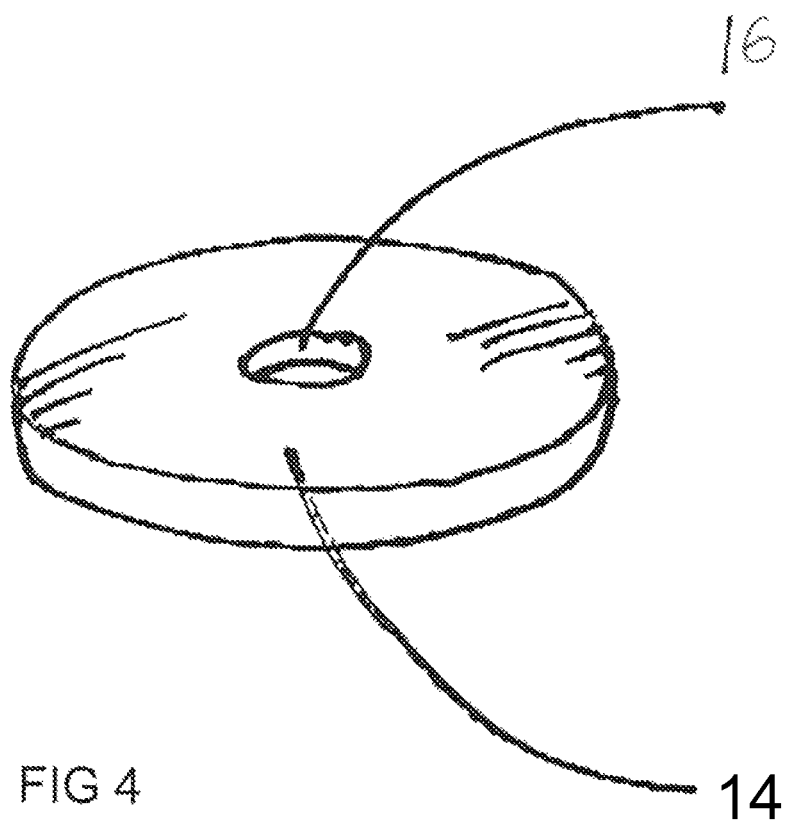
FIG. 4 is a perspective view of the collar.

FIG. 3 shows a hypodermic needle apparatus, generally at 40, inserted in the collar 14. The needle apparatus 40 comprises a plunger 42, a plastic body portion 44 for containing a fluid and a needle portion 46. The plastic body portion 44 has a first, proximal ridge 44a located close to the needle portion 46, and a second, distal ridge 44b located further along the body portion 44. When the needle 40 is placed within the collar 14, a needle portion 42 of the needle apparatus 40 passes through the collar 14 up to the second ridge 44b. Collar 14 has a circular collar opening 16 (shown better in FIG. 4). The collar opening 16 has a slightly bigger circumference than the first ridge 44a of the needle apparatus 40 and a slightly smaller opening than the second ridge 44b of needle apparatus 40. As a consequence of this, when the needle portion 46 is placed through the collar opening 16 of the collar 14, the body portion 44 of the needle apparatus 40 fully covers the collar opening 16. When an operative places the needle portion 46 into the housing 12 and presses down on collar 14 so that the needle portion contacts the electrodes, the microprocessor 18 detects a voltage drop across the electrodes and turns on DC motor 24. The DC motor 24 drives the cutter 22 as will be described below.

Figure 5:
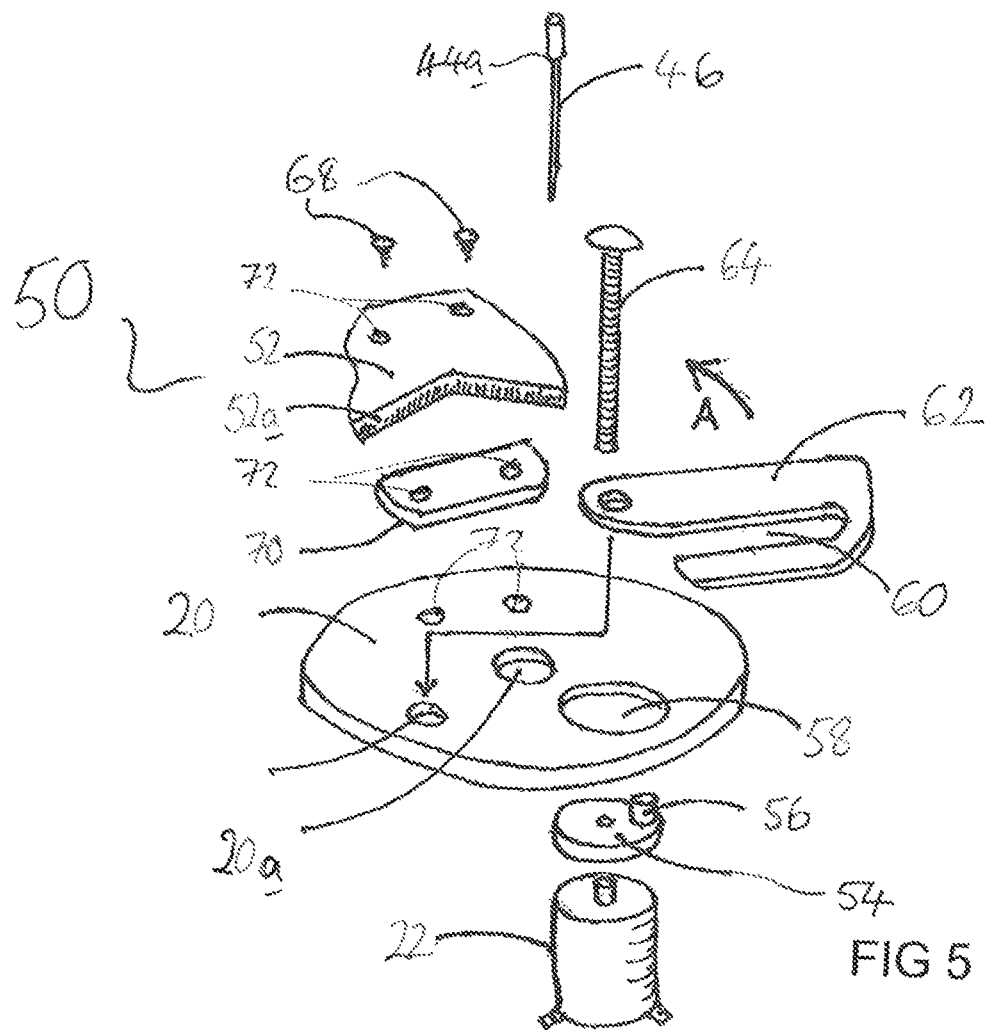
FIG. 5 is an exploded view of the parts of the invention around a mounting plate.

FIG. 5 is a detailed exploded view of the components of the device around the mounting plate 20 which comprises a needle cutting portion of the device. When the needle portion 46 is placed within the housing 12 through collar 14, the needle portion 46 passes through an opening 20a within the mounting plate 20. A cutting assembly shown generally at 50 mounted on the mounting plate 20 is arranged to cut off the needle portion 46 of the needle apparatus 40. The needle apparatus 40 is cut between the first ridge 44a and the second ridge 44b. The needle portion 46 itself is cut from the needle apparatus 40 by pressing it against a stationary cutting blade 52. The DC motor 22 turns a cam assembly 54. A cam stud 56 on the cam assembly 54 passes through a cam opening 58 in mounting plate 20. The cam stud 56 fits within slot 60 in a moveable cutting plate 62 which itself is attached to the mounting plate 20 by a mounting bolt 64 passing through a mounting bolt opening 66. The movable cutting plate 62 is mounted for rotational movement around mounting bolt 64. The stationary cutting blade 52 has a cutting edge 52a and is fixedly mounted on mounting plate 20 by screws 68 via a spacer 70. Spacer 70 is approximately the same thickness as movable cutting plate 62. Pairs of openings 72 in blade 52, spacer 70 and mounting plate 20 are aligned such that screws 68 can be placed through the openings 72 in the blade 52 and spacer 70 and attach the blade 52 and spacer 70 to the mounting plate 20.

When the needle apparatus 40 is placed into the device 10, the needle portion 46 passes through opening 20a in the mounting plate 20. When the needle apparatus 40 contacts oppositely connected electrodes the microprocessor 18 turns on the DC motor 22 which begins to move the movable cutting blade 62 towards the needle. The movable cutting blade 62 makes contact with the needle and pushes it towards the stationary cutting blade 52. The movable cutting blade 62 in combination with the stationary cutting blade 52 severs the needle apparatus between the first ridge 44a and second ridge 44b.

The device 10 has an electrode assembly 24 (shown in FIG. 2) below the mounting plate 20. The electrode assembly comprises a series of circular electrodes which are vertically spaced. The electrodes, alternate ones of which are positive and negative, are vertically spaced and slightly offset horizontally. Each has an aperture at its centre which features a sloping contact surface. When an individual places the needle apparatus 40 into the collar 14 and presses down the bottom of the needle portion 46 makes initial contact with the electrodes. Because of the shape and offset positioning of the electrodes a needle portion must make contact with adjacent oppositely charged electrodes as it travels downwards into the device. When the needle portion 46 makes contact with the both positive and negative electrodes electric current flows through the needle portion 46. The needle portion 46 is of hollow steel and has a high electrical resistance. Because of this the needle will heat up quickly. The needle portion 46 will heat to a temperature at which it will disintegrate. The ash from the disintegrated needle falls through the electrodes and into the removable debris container 32. at the bottom of the device. A plastic stub portion or remnant of the needle 40 severed from the main body 44 will also become disintegrated by the electrodes 24 and fall into the container 32.

Electric power to run the DC motor 22, the electrodes 24 and UV lamp 30 is provided by batteries 26. The batteries 26 in the preferred embodiment are rechargeable metal hydride batteries. and are connected to a recharging circuit (not shown). The recharging circuit is connected to a charging plug 70 on an outer surface of the housing 12.

Figure 6:
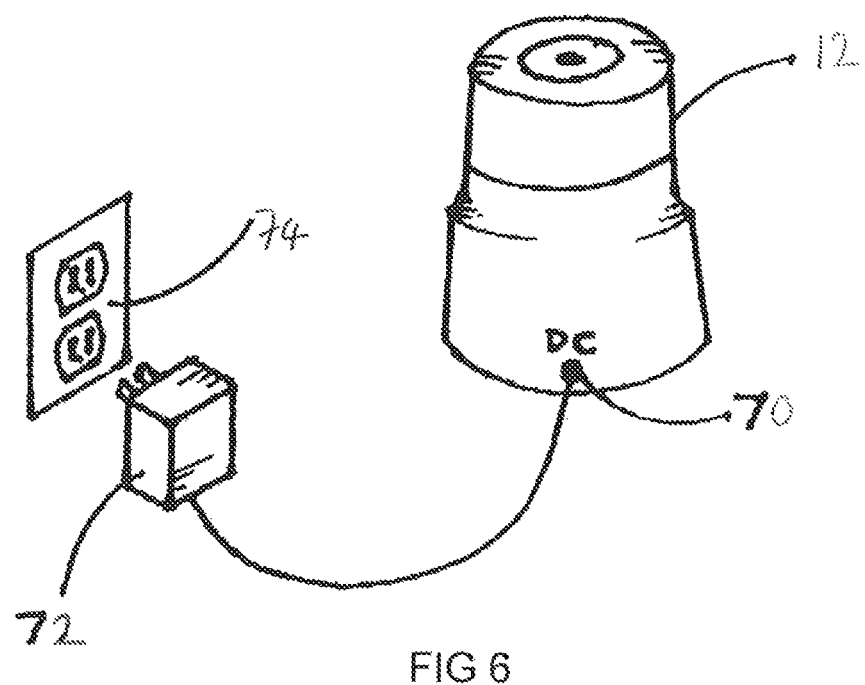
FIG. 6 is a view of the device plugged into a wall socket for recharging.

Turning to FIG. 6, this shows a transformer recharger 72 connected to a wall-mounted mains electrical socket 74 and to charging plug 70. In this configuration the batteries 26 can be recharged using mains electricity.

Inside the device at a lower region is a small ultraviolet light 30 which is configured to radiate into the removable debris container 30. The ultraviolet light from lamp 32 will kill any bacteria, viruses, or disease germs within the container 30. When the transformer recharger 72 is connected to the device and the batteries 26 are recharging, the ultraviolet lamp 30 is arranged to be activated. The ultraviolet light then sterilizes the inside of the device.

Figure 7:
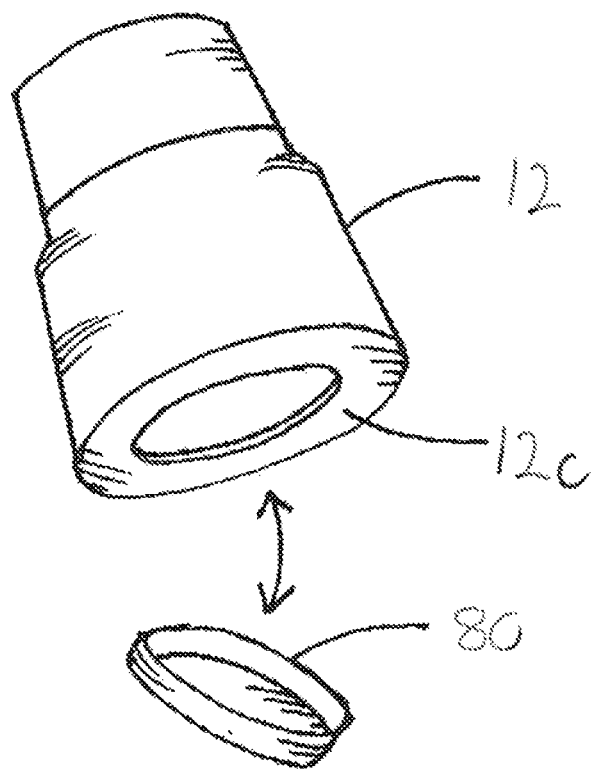
FIG. 7 is a perspective view of an underside of the device.

FIG. 7 is a perspective view of the housing 12 showing an underside 12c thereof. On the underside 12c of the housing 12 is a removable closure 80 which can be removed when the device is not in use to provide access to the removable debris container 32 so that it can be emptied and cleaned.

As described above, the needle apparatus 40, when placed within the collar opening 14, fully closes the collar opening 14. Thus, any sparking that may occur when the needle is disintegrated is kept completely within the device.

Figure 8:
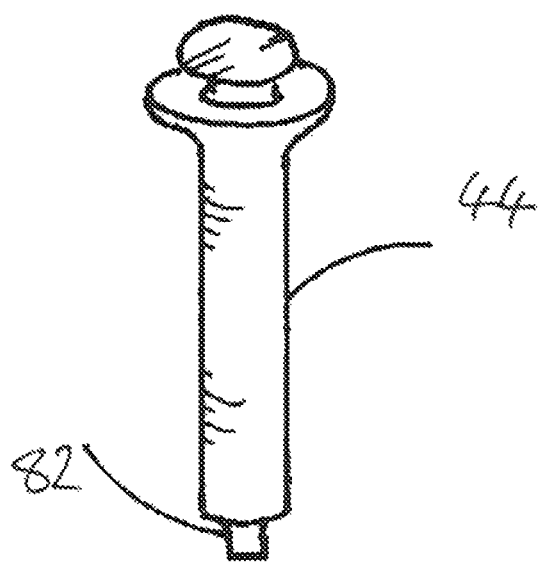
FIG. 8 is a view of a hypodermic needle after a needle end portion has been severed.

FIG. 8 shows what remains of the needle apparatus 40 after the needle portion 46 has been severed from the body 44 of the needle 40. What remains is a harmless part of the body 44 having a small stub 82 which is neither hot nor sharp. The remaining plastic body portion 44 can be thrown in the medical trash and does not have to be disposed of using a specialist sharps container.

In the embodiment described above the disintegration of the needle portion takes place after it becomes severed from the rest of the needle apparatus. However, in other embodiments of the invention the destruction of the needle portion may begin prior to severing it from the rest of the needle apparatus. In these embodiments the needle portion may become severed after a predetermined time or when a trigger condition is detected, such as the needle apparatus has been pushed into the device to a predetermined extent. In such embodiments advantageously the electrodes remain energized temporarily after severance of the needle portion, so that a stub or remnant of the needle portion becomes completely destroyed. This is also useful in the case of very short needles which may not travel sufficiently far into the device for the needle portion to become disintegrated before the cutter is activated.

An advantage of the microprocessor controlled cutter is that it allows a user to operate the device with only one hand, since disintegration of the needle portion and cutting of any stub or remnant takes place automatically as the needle apparatus is pushed into the device without requiring further action from the user.

Figure 9:
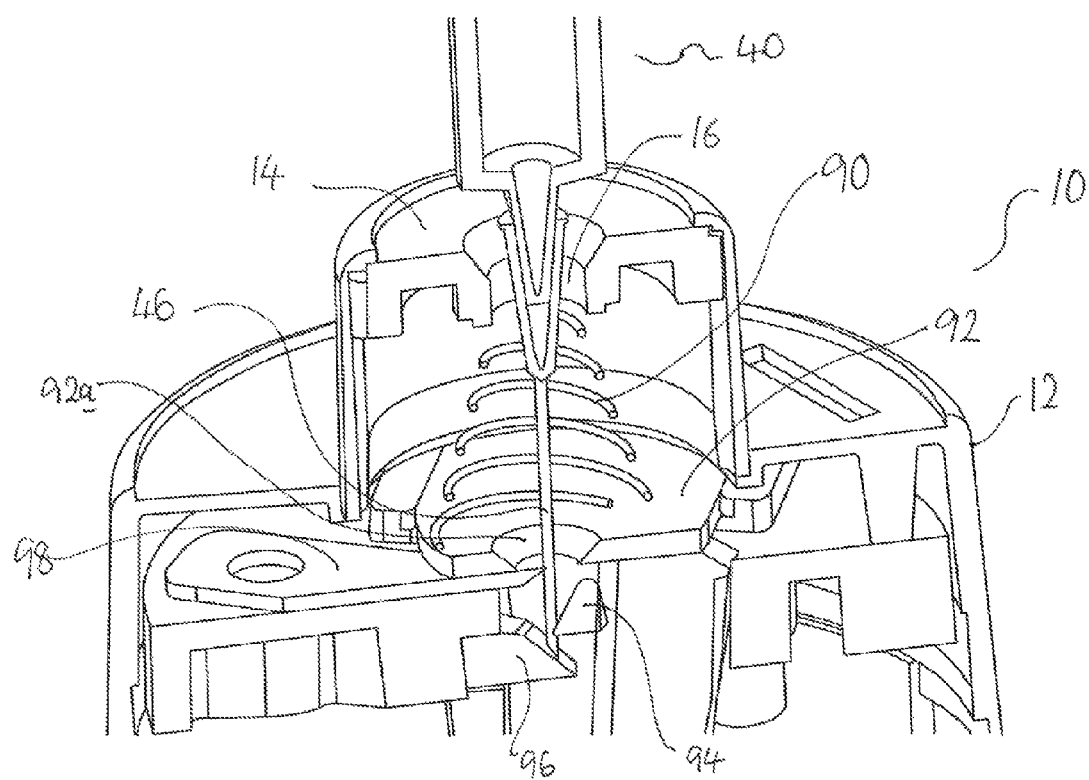
FIG. 9 shows in schematic cross section a part of a second embodiment of needle apparatus disabling device, in accordance with the invention.

Turning to FIG. 9, this shows in schematic sectional view a part of a second embodiment of needle apparatus disabling device, in accordance with the present invention. The lower portion of the needle apparatus is shown generally at 40 with the needle portion 46 inserted in the housing 12 of the device 10.

The collar 14 is mounted for resilient sliding motion within the housing 12 on a coil spring 90. As the needle apparatus is pushed downwards by an operative the second ridge 44b of the needle apparatus 40 will bear against the collar, sealing the collar opening 16 and pushing the collar 14 downwardly against the spring 90 which at its lower end bears against a stationary cutter blade 92.

The needle portion 46 projects through an aperture 92a in the stationary cutter 92 and as it is pushed further into the device it first contacts upper electrode 94 and then lower electrode 96. In this embodiment the electrodes differ from the circular ones shown in FIG. 2 and are generally block shaped. As with the embodiment of FIG. 2, the electrodes have sloping contact faces and are oppositely charged and spaced vertically. They are also offset in a horizontal direction such that as the needle portion 46 passes through the aperture 92a of the stationary cutter 92 the needle portion must contact both electrodes. A current of approximately 30 amps is made to pass through the needle portion, which causes it to become heated resistively to destruction. The needle portion 46 contacting both electrodes also triggers a voltage drop between the electrodes which is detected by the processor (not shown). The processor activates a motor driven movable cutter blade 98 which then severs a remaining stub or remnant of the needle portion and simultaneously urges the severed stub downwardly onto the electrodes 94 and 96 to ensure its complete destruction. During this process any sparks or airborne contaminants, or combustion gases are prevented from escaping through the opening 16 by the sealing action of the second ridge 44b of the needle apparatus 40.

Figure 10:
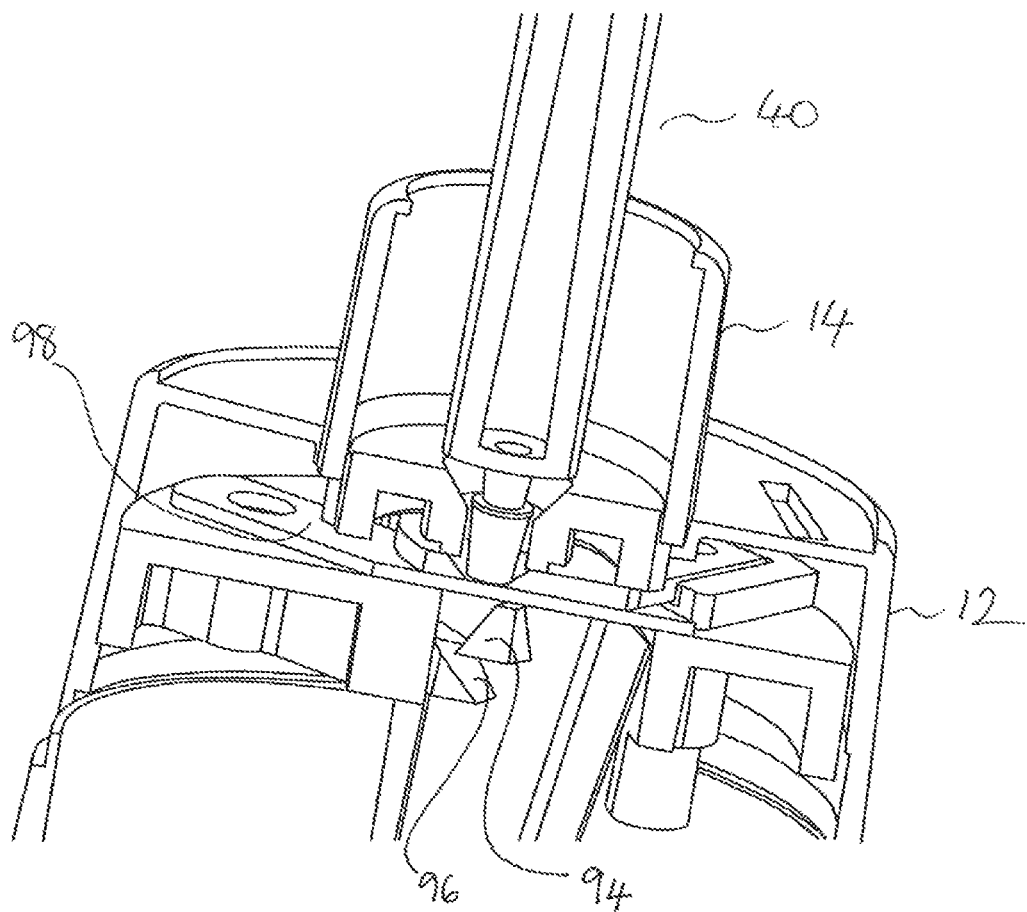
FIG. 10 shows in schematic cross section part of the device of FIG. 9 in an alternative configuration.

FIG. 10 shows in schematic sectional view the device 10 after the moveable cutter has severed the stub of the needle portion and the needle portion has been completely disintegrated. The spring (90 in FIG. 9) has been omitted in the interests of clarity. At this point the needle apparatus 40 may be safely withdrawn from the device as it no longer has any sharp or hot element and therefore presents no risk to the health or safety of an operative.

Figure 11:
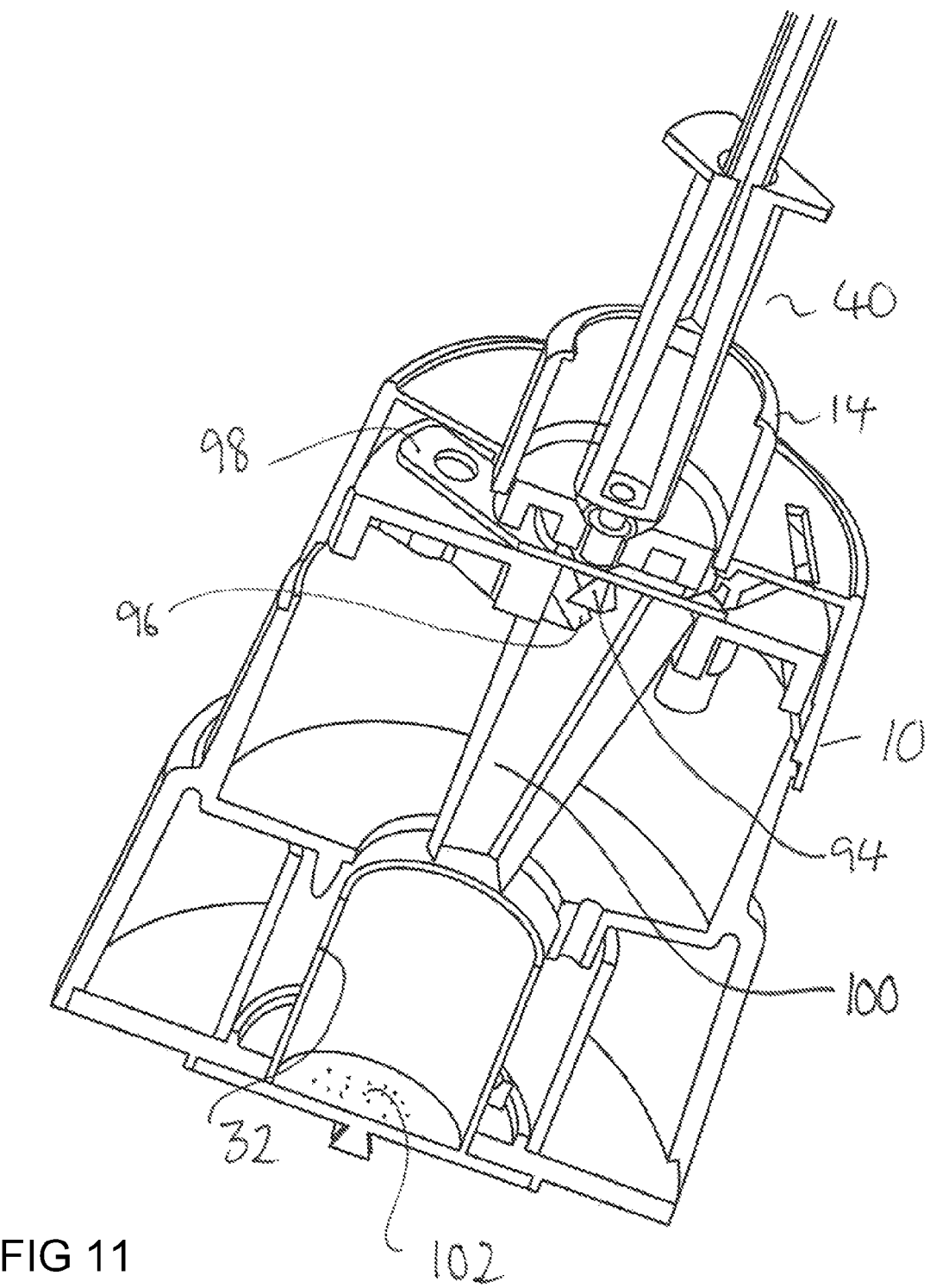
FIG. 11 shows in schematic cross section substantially the entire device of FIGS. 9 and 10.

FIG. 11 is a schematic sectional view of the entire device shown in FIGS. 9 and 10. Below the electrodes 94 and 96 is an elongate debris chute 100 which conducts the falling debris 102 from the destruction of the needle portion to a removable debris container 32 which is generally of cylindrical shape. The debris chute 100 seals to the top mounting plate 20 and forms a tight seal with the bottom plate 101 and extends into the debris container 32 to the extent that debris will remain in the container 32 in event of tipping or displacement of the device.

Whilst endeavouring in the foregoing specification to draw attention to those features of the invention believed to be of particular importance, it should be understood that the applicant claims protection in respect of any patentable feature or combination of features referred to herein, and/or shown in the drawings, whether or not particular emphasis has been placed thereon.

We claim:

1. A needle apparatus disabling device for disabling a needle apparatus having a plastic body portion and a needle portion with a needle and said needle portion contains the entire metal segment of the needle, comprising;
   a. a housing for receiving at least a part of a the needle apparatus,
   b. a means for cutting the needle apparatus that cuts through the plastic body portion above the needle to form a main body portion and a second stub portion attached to the needle portion which contains the entire metal segment of the needle,
   c. an electrode assembly comprises of at least a pair of electrodes for substantially disintegrating the second stub portion and the needle portion of the needle apparatus,
   d. a container for capturing debris.

2. A needle apparatus disabling device according to claim 1 wherein the electrode assembly is supplied current by a series of electrical pulses.

3. A needle apparatus disabling device according to claim 1, wherein the means for cutting the needle apparatus is a cutter comprising:
   a a blade;
   b a motor that drives the blade that cuts through the plastic body portion to form the main body portion and the second stub portion attached to the needle portion which contains the entire metal segment of the needle.

4. A needle apparatus disabling device according to claim 3 wherein the electrode assembly positioned beneath the cutter, such that when the cutter severs the plastic body portion to form the main body portion and the second stub portion attached to the needle portion which contains the entire metal segment of the needle and the severed second stub portion attached the needle portion is urged into contact with the electrodes by the cutter.

5. A needle apparatus disabling device according to claim 3 wherein the electrode assembly remains energized after operation of the cutter so as to disintegrate completely the needle portion.

6. A needle apparatus disabling device according to claim 3, wherein the cutter is controlled by an electronic processor to sever the plastic body portion to form the main body portion and the second stub portion attached to the needle portion which contains the entire metal segment of the needle.

7. A needle apparatus disabling device according to claim 6, wherein the cutter is controlled by an electronic processor which is arranged to detect a drop in voltage between the electrodes as the needle portion contacts the electrode assembly.

8. A needle apparatus disabling device according to claim 3 wherein the housing has an entrance for receiving the needle apparatus with an aperture which is dimensioned for a snug fit with the plastic body portion of the needle apparatus when the needle apparatus is pushed into the entrance, so that a seal is formed between the needle apparatus and the aperture, said seal substantially prevents the escape of any sparks or airborne material from the aperture.

9. A needle apparatus disabling device according to claim 8 wherein the entrance comprises a resiliently biased collar member.

10. A method of disabling a needle apparatus which has a plastic body portion and a needle portion and said needle portion contains the entire metal segment of the needle, comprising the steps of
   a. inserting at least a part of the needle apparatus into a housing,
   b. severing the plastic body portion to form a main body portion and a second stub portion attached to the needle portion which contains the entire metal segment of the needle
   c. disintegrating the second stub portion with the a needle portion of the needle apparatus by passing an electric current from electrodes through the needle portion in an electrode assembly, and
   d. capturing debris in a container in the housing.

11. A method of disabling a needle apparatus which has the plastic body portion and the needle portion with the needle and said needle portion contains the entire metal segment of the needle as in claim 10, wherein the electrode assembly is supplied current by a series of electrical pulses.

12. A method of disabling a needle apparatus which has the plastic body portion and the needle portion with the needle and said needle portion contains the entire metal segment of the needle as in claim 10, wherein the housing has an entrance for receiving the needle apparatus with an aperture which is dimensioned for a snug fit with the plastic body portion of the needle apparatus when the needle apparatus is pushed into the entrance, so that a seal is formed between the needle apparatus and the aperture, said seal substantially prevents the escape of any sparks or airborne material from the aperture.

13. A method of disabling a needle apparatus which has the plastic body portion and the needle portion with the needle and said needle portion contains the entire metal segment of the needle as in claim 12, wherein the entrance comprises a resiliently biased collar member.

14. A method of disabling a needle apparatus which has the plastic body portion and the needle portion with the needle and said needle portion contains the entire metal segment of the needle as in claim 10, wherein the severing is done by a mechanical cutter.

15. A method of disabling a needle apparatus which has the plastic body portion and the needle portion with the needle and said needle portion contains the entire metal segment of the needle as in claim 14, wherein the mechanical cutter is controlled by an electronic processor to sever the plastic body portion to form the main body portion and the second stub portion attached to the needle portion which contains the entire metal segment of the needle.

16. A method of disabling a needle apparatus which has the plastic body portion and the needle portion with the needle and said needle portion contains the entire metal segment of the needle as in claim 14, wherein the mechanical cutter is controlled by an electronic processor which is arranged to detect a drop in voltage between the electrodes as the needle portion contacts the electrode assembly.

17. A method of disabling a needle apparatus which has the plastic body portion and the needle portion with the needle and said needle portion contains the entire metal segment of the needle as in claim 14, wherein the electrode assembly positioned beneath the mechanical cutter, such that when the mechanical cutter severs the plastic body portion to form the main body portion and the second stub portion attached to the needle portion which contains the entire metal segment of the needle and the severed stub portion attached to the needle portion is urged into contact with the electrodes by the cutter.

18. A method of disabling a needle apparatus which has the plastic body portion and the needle portion with the needle and said needle portion contains the entire metal segment of the needle as in claim 14, wherein the electrode assembly remains energized after operation of the mechanical cutter so as to disintegrate substantially completely the stub portion with the needle portion.

\* \* \* \* \*